(12) United States Patent
Hagiwara

(10) Patent No.: US 7,379,534 B2
(45) Date of Patent: May 27, 2008

(54) X-RAY CT IMAGE PRODUCTION METHOD AND X-RAY CT SYSTEM

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/979,616

(22) Filed: Nov. 2, 2004

(65) Prior Publication Data

US 2005/0094759 A1  May 5, 2005

(51) Int. Cl.
  *G01N 23/083* (2006.01)
  *G01N 23/04* (2006.01)

(52) U.S. Cl. .......................................... 378/901; 378/4

(58) Field of Classification Search ............... 378/4, 378/15, 19, 21, 23, 98, 150, 901
See application file for complete search history.

(56) References Cited

U.S. PATENT DOCUMENTS

| | | | | |
|---|---|---|---|---|
| 5,544,212 A | * | 8/1996 | Heuscher | 378/15 |
| 5,663,995 A | * | 9/1997 | Hu | 378/15 |
| 5,818,896 A | * | 10/1998 | Hsieh | 378/15 |
| 5,825,842 A | | 10/1998 | Taguchi | |
| 5,991,356 A | | 11/1999 | Horiuchi et al. | |
| 6,061,421 A | | 5/2000 | Hagiwara | |
| 6,072,851 A | * | 6/2000 | Sivers | 378/15 |
| 6,104,775 A | * | 8/2000 | Tuy | 378/4 |
| 6,108,575 A | * | 8/2000 | Besson | 600/425 |
| 6,178,220 B1 | * | 1/2001 | Freundlich et al. | 378/4 |
| 6,301,325 B1 | | 10/2001 | Besson et al. | |
| 6,442,228 B1 | | 8/2002 | Woloschek et al. | |
| 6,445,764 B2 | | 9/2002 | Gohno et al. | |
| 6,463,118 B2 | | 10/2002 | Besson | |
| 6,539,074 B1 | | 3/2003 | Yavuz et al. | |
| 6,650,727 B2 | | 11/2003 | Kuroda | |

(Continued)

FOREIGN PATENT DOCUMENTS

EP  0 969 414 A2  1/2000

(Continued)

OTHER PUBLICATIONS

Schaller, et al., Spiral Interpolation Algorithm for Multislice Spiral CT—Part I: Theory, Sep. 2000, IEEE Transactions on Medical Imaging, vol. 19, No. 9, pp. 822-834.*

(Continued)

*Primary Examiner*—Edward J. Glick
*Assistant Examiner*—Anastasia S. Midkiff
(74) *Attorney, Agent, or Firm*—Armstrong Teasdale LLP

(57) ABSTRACT

A method to reconstruct an image by utilizing a plurality of projection data items acquired with X-rays that pass through the same pixel location in the same scan field while being transmitted along different paths with a scanner gantry set at the same view angle or an opposite view angle. A helical scan is performed in order to acquire projection data. Two or more projection data items acquired with X-rays that pass through a pixel location Q in the scan field while being transmitted along different paths with the scanner gantry set at the same view angle are synthesized in order to produce reconstruction projection data. A CT image is reconstructed based on the reconstruction projection data.

16 Claims, 14 Drawing Sheets

U.S. PATENT DOCUMENTS

| | | |
|---|---|---|
| 6,744,844 B2 | 6/2004 | Horiuchi |
| 6,765,983 B2 * | 7/2004 | Yan et al. ................. 378/8 |
| 6,775,346 B2 * | 8/2004 | Heuscher et al. ............ 378/4 |
| 6,795,522 B2 | 9/2004 | Nishide et al. |

FOREIGN PATENT DOCUMENTS

| | | |
|---|---|---|
| JP | 09-019425 | 1/1997 |
| JP | 9313472 | 12/1997 |
| JP | 2002-066420 | 3/2002 |
| JP | 2002-147061 | 5/2002 |
| JP | 2002-147231 | 5/2002 |
| JP | 2002-235561 | 8/2002 |
| JP | 2002-235662 | 8/2002 |
| JP | 2002-267833 | 9/2002 |
| JP | 2002-322756 | 11/2002 |
| JP | 2002-338947 | 11/2002 |
| JP | 2003-159244 | 6/2003 |

OTHER PUBLICATIONS

Schaller, et. al., New efficient Fourier-reconstruction method for approximate image reconstruction in spiral cone-beam CT at small cone angles, 1997, SPIE, vol. 3032, pp. 213-224.*

EP Partial Search Report; Place of Search The Hague; App. No. 04 256 828.7; Jul. 26, 2005 Date of Search; 4 pgs.

Margaret E. Daube-Witherspoon, et al.; Treatment of Axial Data in Three-Dimensional PET; The Journal of Nuclear Medicine 28:1717-1724 (1987); ppp. 1717-1724.

Stefan Schaller, et al.; New, efficient Fourier-reconstruction method for approximate image reconstruction in spiral cone-beam CT at small cone angles; SPIE vol. 3032, 0277-786X/97; XP-000996742 (1997); pp. 213-224.

Frederic Noo, et al.; Single-slice rebinning method for helical cone-beam CT; Phys. Med. Biol. 44 (1999); pp. 561-570.

Hui Hu; Multi-slice helical CT: Scan and reconstruction; Medical Physics, vol. 26, No. 1 (Jan. 1999); pp. 5-18.

Stefan Schaller, et al.; Spiral Interpolation Algorithm for Multislice Spiral CT—Part I : Theory; IEEE Transactions on Medical Imaging, vol. 19, No. 9 (Sep. 2000); pp. 822-834.

EP Search Report; European Patent Office Rijswijk; Reference 156284/10357; App. No. 04256828.7; Jan. 5, 2006 Date of Search; 6 pgs.

Stierstorfer, et al.; Segmented Multiple Plane Reconstruction: A Novel Approximate Reconstruction Scheme for Multi-Slice Spiral CT; Phys. Med. Biol. 47, (2002), pp. 2571-2581.

Schaller, et al.; New, Efficient Fourier-Reconstruction Method for Approximate Image Reconstruction in Spiral Cone-Beam CT at Small Cone Angles; Proceedings of the Spie, Spie, Bellingham, VA, US, vol. 3032, Feb. 1997, pp. 213-224.

* cited by examiner

START CT image production
↓
Perform helical scan — S1
↓
Perform pre-processing — S2
↓
Execute image production — S3
↓
Perform post-processing — S4
↓
END

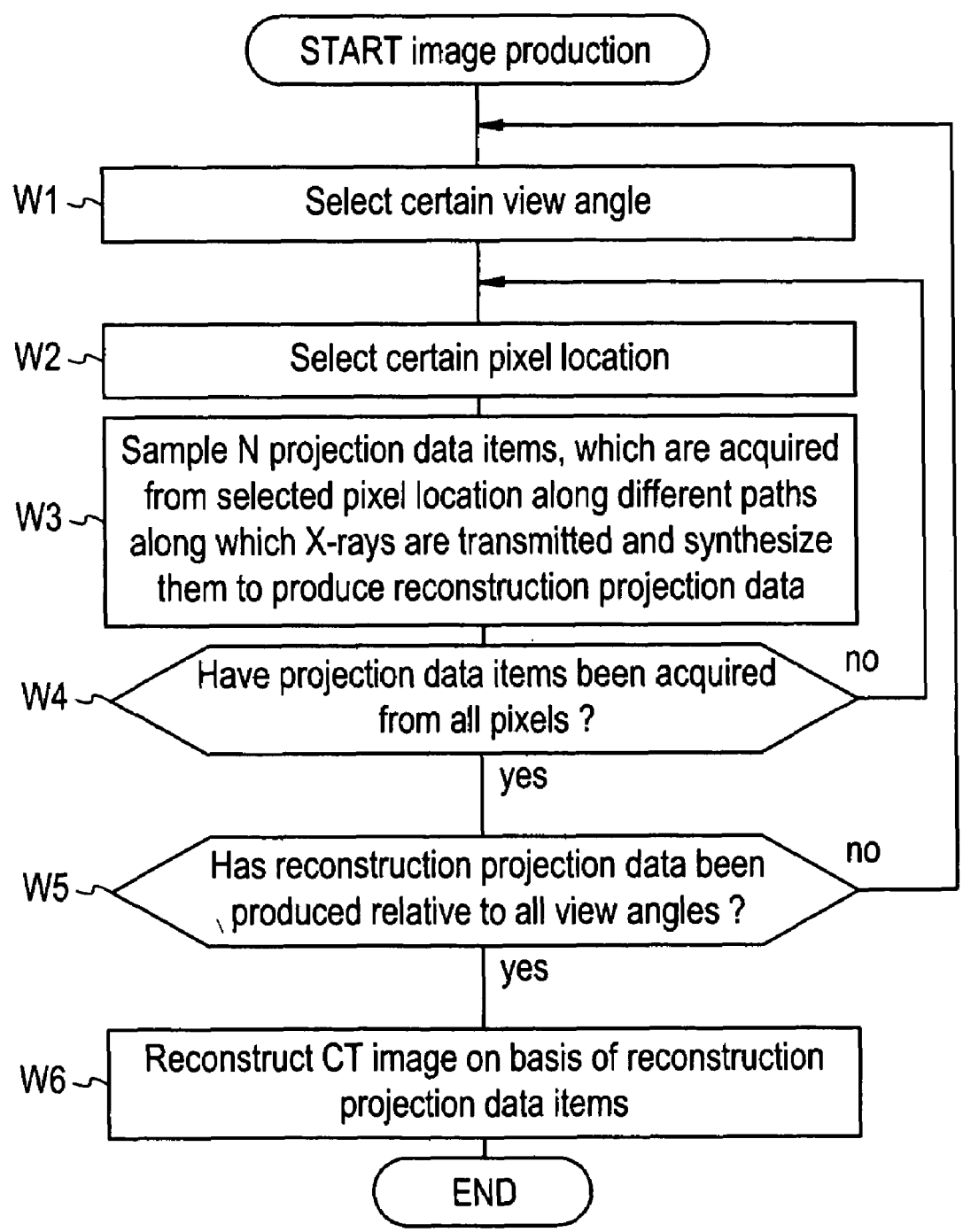

view = 720° view = 1080°

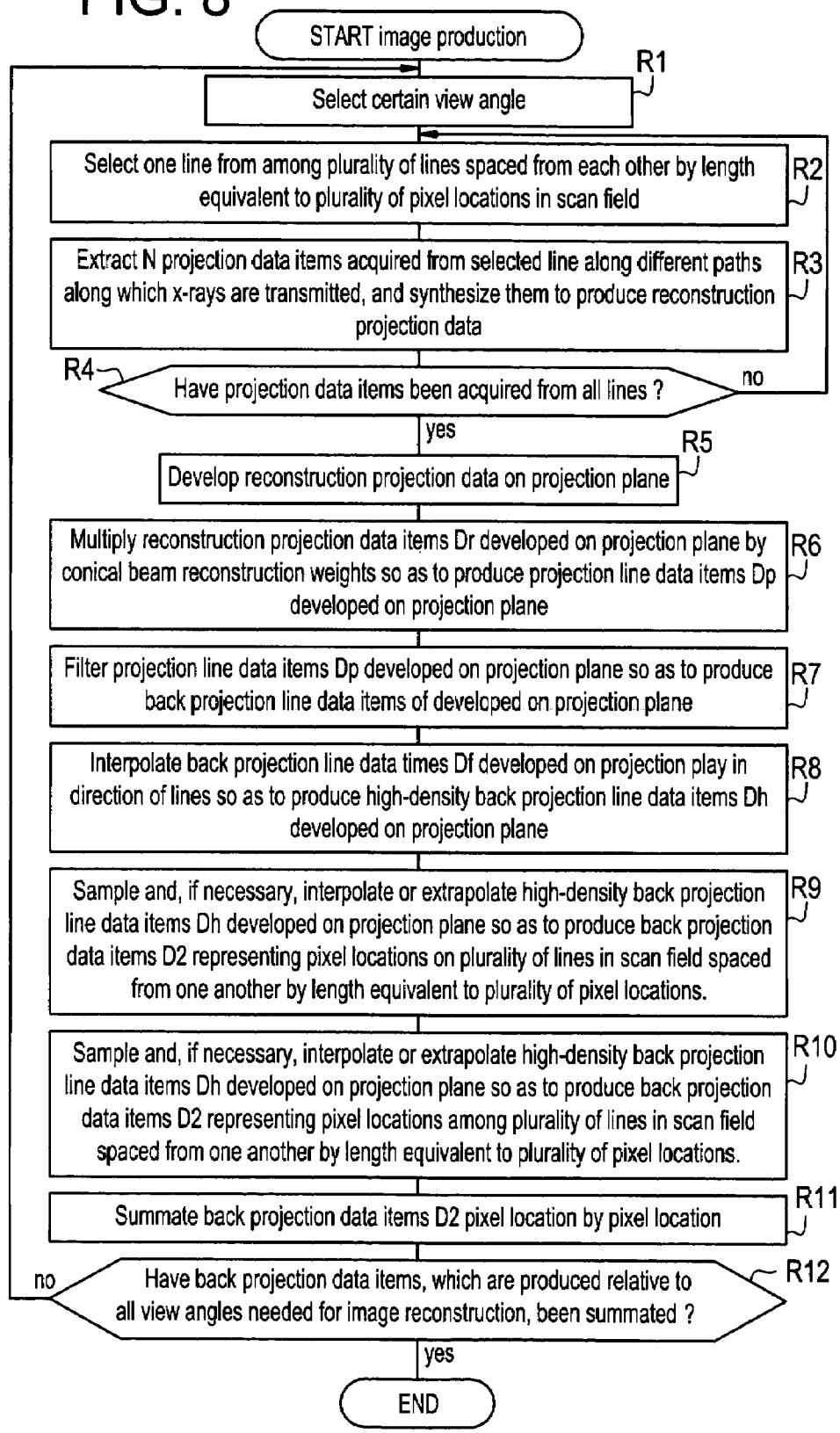

X-RAY CT IMAGE PRODUCTION METHOD AND X-RAY CT SYSTEM

CROSS REFERENCE TO RELATED APPLICATIONS

This application claims the benefit of Japanese Application No. 2003-373892 filed Nov. 4, 2003.

BACKGROUND OF THE INVENTION

The present invention relates to an X-ray computed tomography (CT) image production method and an X-ray CT system. More particularly, the present invention is concerned with an X-ray CT image production method and an X-ray CT system that reconstruct an image by utilizing a plurality of projection data items acquired with X-rays which pass through the same pixel location in the same scan field while being transmitted along different paths with a scanner gantry set at the same view angle or an opposite view angle.

Conventionally, X-ray CT systems are known (refer to, for example, Patent Document 1) to be such that: projection data is acquired while an X-ray tube and a multi-channel detector are rotated about a subject and a tabletop on which the subject lies down is rectilinearly moved; projection data items acquired with X-rays that pass through a pixel location in a scan field are sampled in order to produce a data set that is used to reconstruct a CT image expressing the scan field; and a CT image is then reconstructed based on the data set.

[Patent Document 1] Japanese Unexamined Patent Application Publication No. 2003-159244.

When a helical scan is performed using a multi-channel detector, a plurality of projection data items is acquired using X-rays that pass through the same pixel location in the same scan field while being transmitted along different paths with a scanner gantry set at the same view angle.

However, the conventional X-ray CT system does not utilize the plurality of projection data items but samples one projection data instead of projection data items that are acquired with the scanner gantry set at a certain view angle, and uses the sampled projection data to reconstruct an image.

SUMMARY OF THE INVENTION

Therefore, an object of the present invention is to provide an X-ray CT image production method and an X-ray CT system that reconstruct an image by utilizing a plurality of projection data items acquired using X-rays which pass through the same pixel location in the same scan field while being transmitted along different paths at a scanner gantry set at the same view angle or an opposite view angle.

According to the first aspect of the present invention, there is provided an X-ray CT image production method. Herein, while at least one of an X-ray tube and a multi-channel detector is relatively rotated about a subject and the subject is relatively rectilinearly moved, projection data is acquired. Two or more projection data items acquired with X-rays that pass through the same pixel location in a scan field while being transmitted along different paths with a scanner gantry set at the same view angle or an opposite view angle are synthesized in order to produce reconstruction projection data relevant to the view angle. A CT image is then reconstructed based on the reconstruction projection data.

In the X-ray CT image production method according to the first aspect, a plurality of projection data items acquired with X-rays that pass through a pixel location in a scan field while being transmitted along different paths with the scanner gantry set at the same view angle or an opposite view angle is sampled from among all projection data items acquired by performing a helical scan using the multi-channel detector. The sampled projection data items are synthesized in order to produce reconstruction projection data. A CT image is reconstructed based on a data set comprising reconstruction projection data items relevant to all view angles needed to reconstruct CT images. Consequently, pieces of information acquired along the two or more paths along which X-rays are transmitted are reflected on data relevant to one view angle. The shape of the subject can be reproduced accurately. Moreover, since the reproduction of the shape brings about little contradiction, artifact can be reduced. Furthermore, since an amount of information increases, a signal-to-noise ratio improves.

According to the second aspect of the present invention, there is provided an X-ray CT image production method identical to the foregoing X-ray CT image production method except that two or more projection data items are weighted and summated in order to product the reconstruction projection data.

In the X-ray CT image production method according to the second aspect, two or more projection data items are weighted and summated for synthesis in order to produce one reconstruction projection data. The quality of an CT image can be adjusted by changing the weights that are used for the weighting and summation.

According to the third aspect of the present invention, there is provided an X-ray CT image production method identical to the foregoing X-ray CT image production method except that as the distances from detector arrays, which detect two or more projection data items respectively, to the scan field is shorter, the weights to be used for the weighting and summation are made larger.

In the X-ray CT image production method according to the third aspect, if the detector arrays having detected the projection data items are located closely to the scan field, the weights to be applied to the projection data items are made larger. If the detector arrays are located far from the scan field, the weights to be applied to the projection data items are made smaller. Consequently, the quality of a CT image can be improved without being changed largely.

According to the fourth aspect of the present invention, there is provided an X-ray CT image production method that is identical to the foregoing X-ray CT image production method except that an operator can designate the weights that are used for the weighting and summation.

In the X-ray CT image production method according to the fourth aspect, an operator can change the weights that are used for the weighting and summation and can eventually adjust the quality of a CT image.

According to the fifth aspect of the present invention, there is provided an X-ray CT image production method that is identical to the foregoing X-ray CT image production method except that an operator can designate the number of projection data items N that is larger than 2.

In the X-ray CT image production method according to the fifth aspect, an operator can change the number of projection data items N that is larger than 2, and can eventually adjust the quality of a CT image.

According to the sixth aspect of the present invention, there is provided an X-ray CT image production method in which: while at least one of an X-ray tube and a multi-channel detector is relatively rotated about a subject and the subject is relatively rectilinearly moved, projection data is acquired; two or more data sets are produced in order to reconstruct a CT image expressing a scan field; two or more CT images are then reconstructed based on the two or more data sets; and the CT images are synthesized to produce a synthetic CT image.

In the X-ray CT image production method according to the sixth aspect, a plurality of projection data items acquired with X-rays that pass through a pixel location in a scan field while being transmitted along different paths with a scanner gantry set at the same view angle or an opposite view angle is sampled from among all projection data items acquired by performing a helical scan using the multi-channel detector. Data sets containing the respective projection data items are produced. CT images are reconstructed based on the respective data sets, and synthesized in order to construct a synthetic CT image. Consequently, since pieces of information acquired along two or more paths along which X-rays are transmitted are reflected on data relevant to one view angle, the shape of the subject can be reproduced accurately. Moreover, since the reproduction of the shape brings about little contradiction, artifact can be reduced. Furthermore, since an amount of information increases, a signal-to-noise ratio improves.

According to the seventh aspect of the present invention, there is provided an X-ray CT image production method identical to the aforesaid X-ray CT image production method except that two or more CT images are weighted and summated in order to construct the synthetic CT image.

In the X-ray CT image production method according to the seventh aspect, two or more CT images are weighted and summated for synthesis in order to construct a new CT image. The quality of the new CT image can be adjusted by changing the weights to be used for the weighting and summation.

According to the eighth aspect of the present invention, there is provided an X-ray CT image production method identical to the foregoing X-ray CT image production method except that as the distances from detector arrays, via which the data sets are produced, to the scan field is shorter, the weights to be used for the weighting and summation are made larger.

In the X-ray CT image production method according to the eighth aspect, if the detector arrays via which the data sets are produced (the detector array located in the center among the plurality of detector arrays) are located closely to the scan field, the weights to be applied to the projection data items are increased. If the detector arrays are located far away, the weights are decreased. Consequently, the quality of a CT image can be improved without being drastically changed.

According to the ninth aspect of the present invention, there is provided an X-ray CT image production method identical to the foregoing X-ray CT image production method except that an operator can designate the weights to be used for the weighting and summation.

In the X-ray CT image production method according to the ninth aspect, an operator can change the weights to be used for the weighting and summation and can eventually adjust the quality of a CT image.

According to the tenth aspect of the present invention, there is provided an X-ray CT image production method identical to the foregoing X-ray CT image production method except that an operator can designate the number of data sets N that is larger than 2.

In the X-ray CT image production method according to the tenth aspect, an operator can change the number of data sets N that is larger than 2 and can eventually adjust the quality of a CT image.

According to the eleventh aspect of the present invention, there is provided an X-ray CT system comprising: an X-ray tube; a multi-channel detector; a helical scan means for acquiring projection data while relatively rotating at least one of the X-ray tube and multi-channel detector about a subject and relatively rectilinearly moving the subject; a reconstruction projection data production means for synthesizing two or more projection data items acquired with X-rays that pass through the same pixel location in a scan field while being transmitted along different paths with a scanner gantry set at the same view angle or an opposite view angle, and thus producing reconstruction projection data relevant to the view angle; and an image reconstruction means for reconstructing a CT image on the basis of the reconstruction projection data.

In the X-ray CT system according to the eleventh aspect, the X-ray CT image production method in accordance with the first aspect can be implemented.

According to the twelfth aspect of the present invention, there is provided an X-ray CT system identical to the foregoing X-ray CT system except that the reconstruction projection data production means weights and summates the two or more projection data items so as to produce the reconstruction projection data.

In the X-ray CT system according to the twelfth aspect, the X-ray CT image production method in accordance with the second aspect can be implemented.

According to the thirteenth aspect of the present invention, there is provided an X-ray CT system identical to the foregoing X-ray CT system except that the reconstruction projection data production means makes the weights, which are used for the weighting and summation, larger as the distances from detector arrays, which detect the two or more projection data items, to the scan field are shorter.

In the X-ray CT system according to the thirteenth aspect, the X-ray CT image production method in accordance with the third aspect can be implemented.

According to the fourteenth aspect of the present invention, there is provided an X-ray CT system identical to the foregoing X-ray CT system except that a designation means is included for allowing an operator to designate the weights to be used for the weighting and summation.

In the X-ray CT system according to the fourteenth aspect, the X-ray CT image production method in accordance with the fourth aspect can be implemented.

According to the fifteenth aspect of the present invention, there is provided an X-ray CT system identical to the foregoing X-ray CT system except that a designation means is included for allowing an operator to designate the number of projection data items N which is larger than 2.

In the X-ray CT system according to the fifteenth aspect, the X-ray CT image production method in accordance with the fifth aspect can be implemented.

According to the sixteenth aspect of the present invention, there is provided an X-ray CT system comprising: an X-ray tube; a multi-channel detector; a helical scan means for acquiring projection data while relatively rotating at least one of the X-ray tube and multi-channel detector about a subject and relatively rectilinearly moving the subject; a data set production means for producing two or more data sets that are used to reconstruct CT images expressing a scan field; an image reconstruction means for reconstructing two or more CT images on the basis of the two or more data sets;

and an image synthesis means for synthesizing the CT images to construct a synthetic CT image.

In the X-ray CT system according to the sixteenth aspect, the X-ray CT image production method in accordance with the sixth aspect can be implemented.

According to the seventeenth aspect of the present invention, there is provided an X-ray CT system identical to the foregoing X-ray CT system except that the image synthesis means weights and summates the two or more CT images so as to construct the synthetic CT image.

In the X-ray CT system according to the seventeenth aspect, the X-ray CT image production method in accordance with the seventh aspect can be implemented.

According to the eighteenth aspect of the present invention, there is provided an X-ray CT system identical to the foregoing X-ray CT system except that as the distances from detector arrays, via which the data sets are produced, to the scan field are shorter, the weights to be used for the weighting and summation are made larger.

In the X-ray CT system according to the eighteenth aspect, the X-ray CT image production method in accordance with the eighth aspect can be implemented.

According to the nineteenth aspect of the present invention, there is provided an X-ray CT system identical to the foregoing X-ray CT system except that a designation means is included for allowing an operator to designate the weights to be used for the weighting and summation.

In the X-ray CT system according to the nineteenth aspect, the X-ray CT image production method in accordance with the ninth aspect can be implemented.

According to the twentieth aspect of the present invention, there is provided an X-ray CT system identical to the foregoing X-ray CT system except that a designation means is included for allowing an operator to designate the number of data sets N that is larger than 2.

In the X-ray CT system according to the twentieth aspect, the X-ray CT image production method in accordance with the tenth aspect can be implemented.

According to an X-ray CT image production method and an X-ray CT system in which the present invention is implemented, the shape of a subject can be accurately reproduced and artifact can be reduced. Moreover, a signal-to-noise ratio can be improved.

An X-ray CT image production method and an X-ray CT system in accordance with the present invention can be used to produce a high-quality X-ray CT image.

Further objects and advantages of the present invention will be apparent from the following description of the preferred embodiments of the invention as illustrated in the accompanying drawings.

BRIEF DESCRIPTION OF THE DRAWINGS

FIG. 6 is a flowchart describing image production employed in the first embodiment.

FIG. 8 is a flowchart describing image production employed in a second embodiment.

DETAILED DESCRIPTION OF THE INVENTION

The present invention will be described in relation to embodiments shown in drawings. Noted is that the present invention shall not be limited to the embodiments.

First Embodiment

Figure 1:
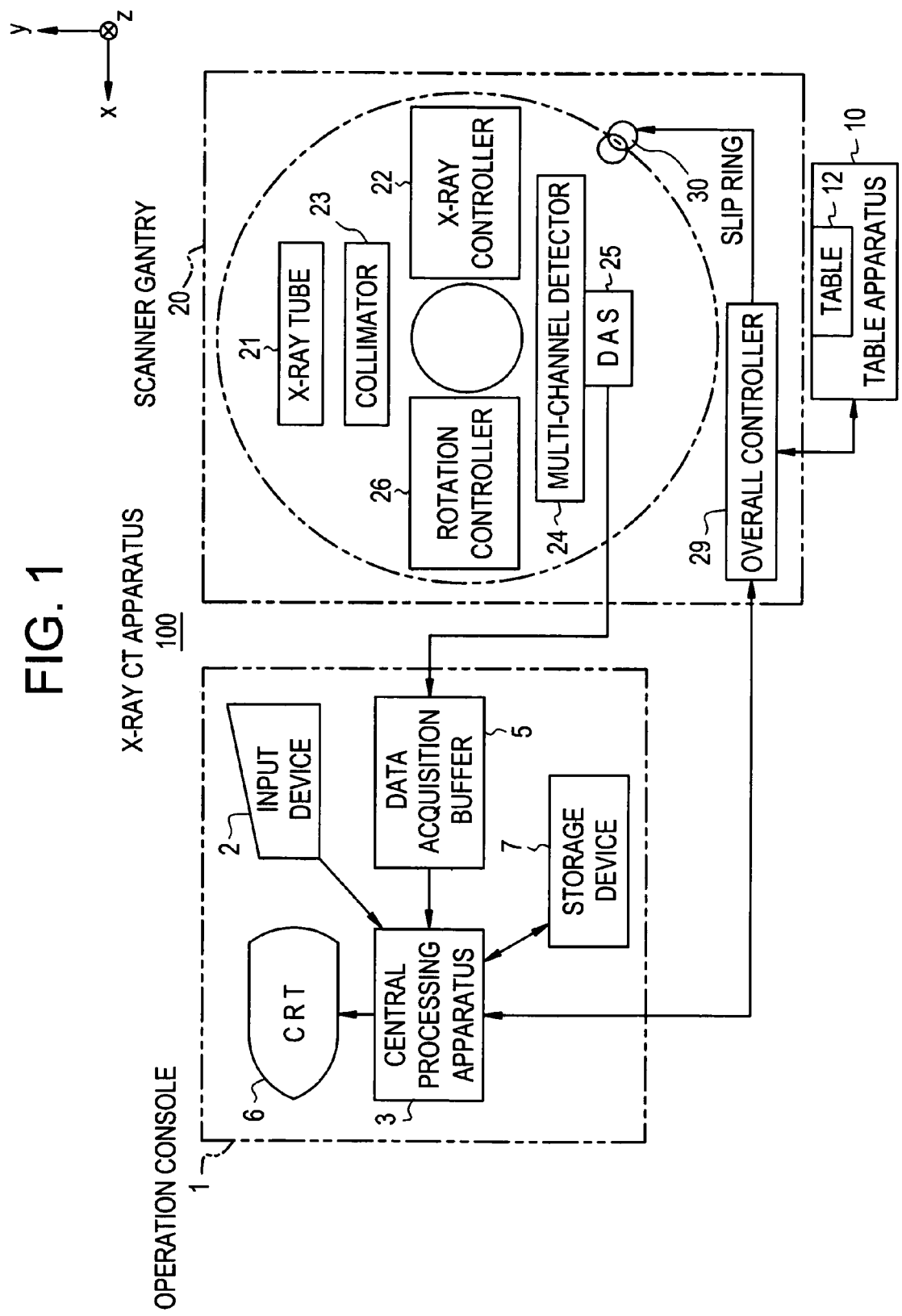
FIG. 1 is a block diagram showing the configuration of an X-ray CT system in accordance with a first embodiment of the present invention.

FIG. 1 is a block diagram showing the configuration of an X-ray CT system in accordance with the first embodiment. An X-ray CT system 100 comprises an operator console 1, a patient couch 10, and a scanner gantry 20. The operator console 1 comprises: an input device 2 that receives an operator's entry; a central processing unit 3 that executes image reconstruction and others; a data acquisition buffer 5 in which projection data acquired by the scanner gantry 20 is stored; a CRT 6 on which a CT image reconstructed based on the projection data is displayed; and a storage device 7 in which programs, data, and X-ray CT images are stored. The patient couch 10 includes a tabletop 12 that is inserted into or withdrawn from a bore of the scanner gantry 20 with a subject lying down thereon. The tabletop 12 is lifted or lowered or rectilinearly moved by a motor incorporated in the patient couch 10. The scanner gantry 20 accommodates an X-ray tube 21, an X-ray controller 22, a collimator 23, a multi-channel detector 24, a data acquisition system (DAS) 25, a rotation controller 26 for controlling the DAS 25, and a control unit 29 that communicates control signals or the like to or from the operator console 1 and patient couch 10, and a slip ring 30.

Figure 2:
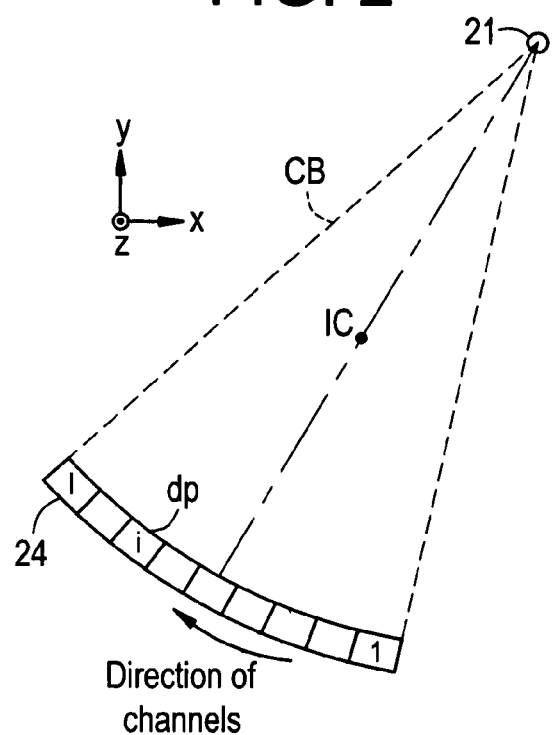
FIG. 2 is an explanatory diagram showing the rotation of an X-ray tube and a multi-channel detector.
Figure 3:
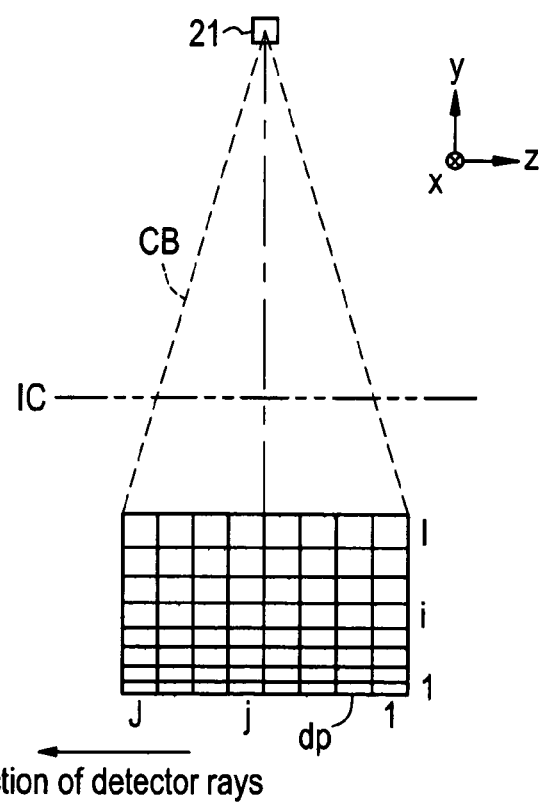
FIG. 3 is an explanatory diagram showing a conical beam.

FIG. 2 and FIG. 3 are explanatory diagrams concerning the X-ray tube 21 and multi-channel detector 24. The X-ray tube 21 and multi-channel detector 24 rotate about a center of rotation IC. The direction of rectilinear movement made by the tabletop 12 shall be a z-axis direction, and the direction perpendicular to the top of the tabletop 12 shall be a y-axis direction, and the direction perpendicular to the z-axis direction and y-axis direction alike shall be an x-axis direction. At this time, the X-ray tube 21 and multi-channel detector 24 rotate on an xy plane. The X-ray tube 21 generates an X-ray beam CB that is a conical beam. When the direction of the center axis of the X-ray beam CB is parallel to the y-axis direction, a view angle view shall be 0°. The multi-channel detector 24 has, for example, 256 detector arrays. The detector arrays provide, for example, 1024 channels.

Figures 4, 5:
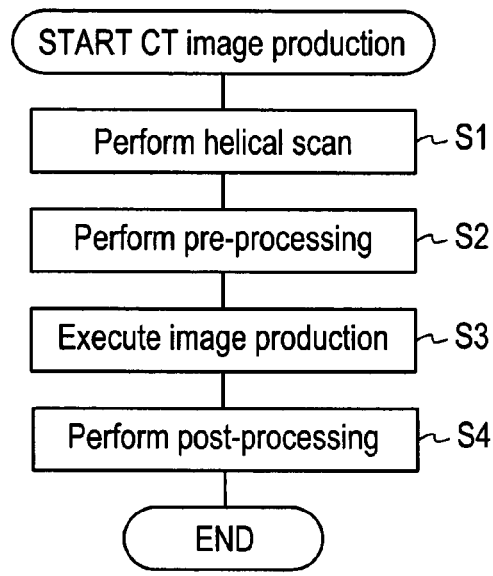
FIG. 4 is a flowchart describing actions to be performed in the X-ray CT system in accordance with the first embodiment.
FIG. 5 is an explanatory diagram showing a data structure.

FIG. 4 is a flowchart describing actions to be performed in the X-ray CT system 100. At step S1, the X-ray tube 21 and multi-channel detector 24 are rotated about a subject and the tabletop 12 is moved rectilinearly. Meanwhile, projection data D0(a, view,j,i) identified with a rectilinear movement end position z, a view angle view, a detector array number j, and a channel number i is acquired. In order to detect the rectilinear movement end position z, that is, a position in the z-axis direction, an encoder is used to count the number of pulses. The control unit 29 converts the count value into a z-coordinate. Eventually, z-coordinate information is appended to projection data acquired by the DAS 25 via the slip ring 30.

FIG. 5 shows the structure of projection data acquired at a certain view angle view. At step S2, pre-processing (offset correction, logarithm correction, X-ray dose correction, and sensitivity correction) is performed on the projection data D0(z, view,j,i). At step S3, a CT image is produced based on the pre-processed projection data D0(z, view,j,i). The image production will be detailed later. At step S4, the produced CT image is post-processed so that it can be appropriately displayed.

FIG. 6 is a flowchart describing the image production (step S3). At step W1, a view angle is selected from among all view angles within a view range needed for image reconstruction (for example, 180°+angle of a fan beam). At step W2, one pixel location is selected from among all pixel locations in a scan field. At step W3, N ($\geq 2$) projection data items acquired with X-rays that pass through the selected pixel location while being transmitted along different paths with the scanner gantry set at the selected view angle or an opposite view angle are sampled from among all projection data items acquired by performing a helical scan. The sampled N projection data items are synthesized in order to produce reconstruction projection data.

For example, as shown in FIGS. 7(a), 7(b), 7(c), and 7(d), while the scanner gantry is rotated by one turn, two turns, three turns, and four turns in order to achieve a helical scan, projection data items acquired with X-rays L1, L2, L3, and L4 that pass through a pixel location Q in a scan field P, also referred to as an image reconstruction plane P, while being transmitted along different paths with the scanner gantry set at the view angle view of 0° (=360°=720°=1080°) are detected by detector arrays 4A, 2A, 2B, and 4B respectively. The four (=N) projection data items detected by the detector arrays 4A, 2A, 2B, and 4B respectively are sampled as projection data items acquired at the view angle of 0°. Thereafter, the projection data items are multiplied by weights w1, w2, w3, and w4 proportional to distances d1, d2, d3, and d4 of the detector arrays 4A, 2A, 2B, and 4B, which detect the sampled projection data items, from the scan field P, and then summated. This results in reconstruction projection data.

For example, the weights w1, w2, w3, and w4 are calculated as follows:

$$wk=(1/dk)/(1/d1+1/d2+1/d3+1/d4)$$

where k denotes 1, 2, 3, or 4.

Moreover, the z-coordinate or the position in the z-axis direction that helps identify reconstruction projection data shall be the position in the z-axis direction at which the X-ray tube is located when projection data is detected by a detector array out of the detector arrays, which detect the plurality of projection data items, whose distance from the scan field P is the shortest.

Incidentally, an operator can use the input device 2 to change the setting of the number of projection data items to be synthesized N or the settings of the weights with which the N projection data items are weighted before they are summated.

At step W4, steps W2 and W3 are repeated relative to all pixel locations in the scan field.

At step W5, steps W1 to W4 are repeated relative to all view angles needed for image reconstruction.

At step W6, a CT image is reconstructed based on a data set comprising reconstruction projection data items relevant to all view angles needed for image reconstruction. An image reconstruction method to be adopted at this time may be a two-dimensional image reconstruction method or a three-dimensional image reconstruction method such as the Feldkamp method or the weighted Feldkamp method.

According to the X-ray CT system 100 of the first embodiment, since pieces of information acquired with X-rays transmitted along two or more different paths are reflected on data relevant to one view angle, the shape of a subject can be reproduced accurately. Moreover, since the reproduction of the shape brings about little contradiction, artifact can be reduced. Furthermore, since an amount of information increases, a signal-to-noise ratio improves.

Second Embodiment

Image production described in FIG. 8 may be executed as step S3 in FIG. 4.

The image production described in FIG. 8 shall be called three-dimensional back projection.

At step R1, a view angle is selected from among all view angles within a view range needed for image reconstruction.

At step R2, a line is selected from among a plurality of parallel lines spaced from one another by a length equivalent to a plurality of pixel locations in the scan field P.

Figure 9A:
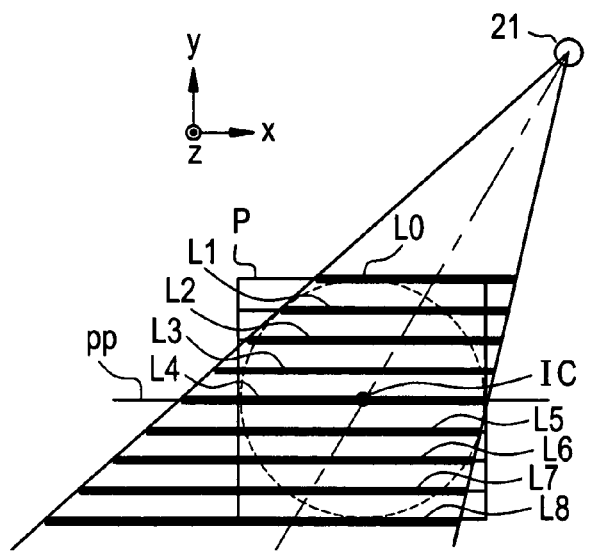
FIG. 9 is a conceptual diagram showing a state in which lines in a scan field P are projected in an X-ray transmitting direction in which X-rays are transmitted.
Figure 9B:
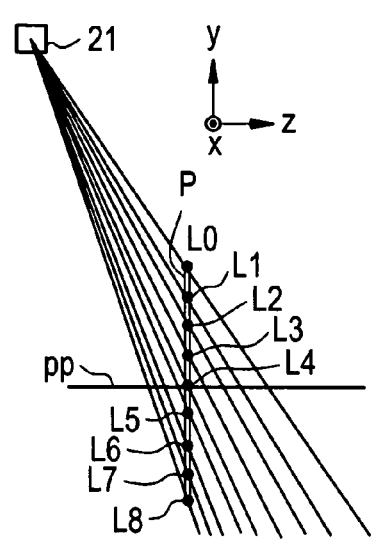

FIG. 9a and FIG. 9b show a an example of a plurality of parallel lines L0 to L8 in the scan field P.

The number of lines is a 1/64 to a 1/2 of the largest number of pixel locations in the scan field P in a direction orthogonal to the lines. For example, when the number of pixel locations in the scan field P is a product of 512 by 512, the number of lines is nine.

Moreover, when a view angle is equal to or larger than −45° and smaller than 45° (or falls within a range centered on the range of view angles) or when the view angle is equal to or larger than 135° and smaller than 225° (or falls within a range centered on the range of view angles), the x-axis direction shall be the direction of lines. Moreover, when the view angle is equal to or larger than 45° and smaller than 135° (or falls within a range centered on the range of view angles) or when the view angle is equal to or larger than 225° and smaller than 315° (or falls within a range centered on the range of view angles), the y-axis direction shall be the direction of lines.

Figure 7A:
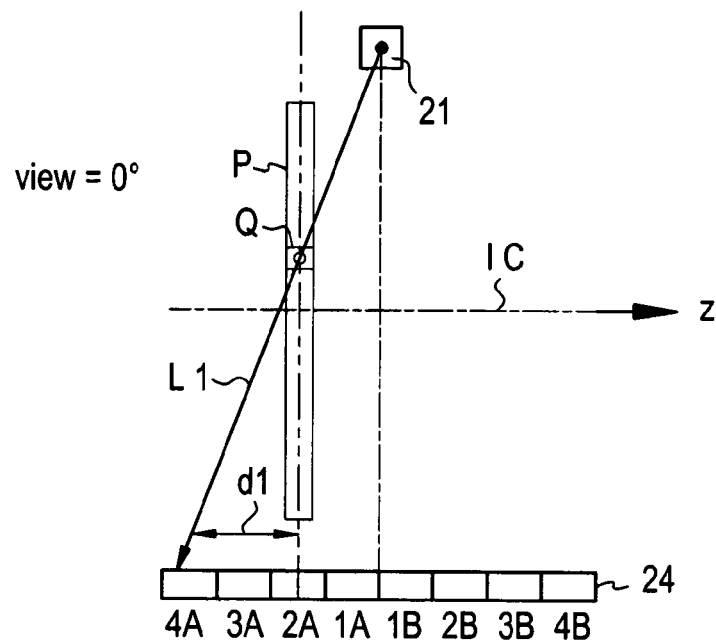
FIG. 7 is an explanatory diagram showing states which are equivalent to a state attained with a scanner gantry set at a view angle view of 0° and in which a plurality of projection data items is acquired from one pixel location in a scan field.
Figure 7B:
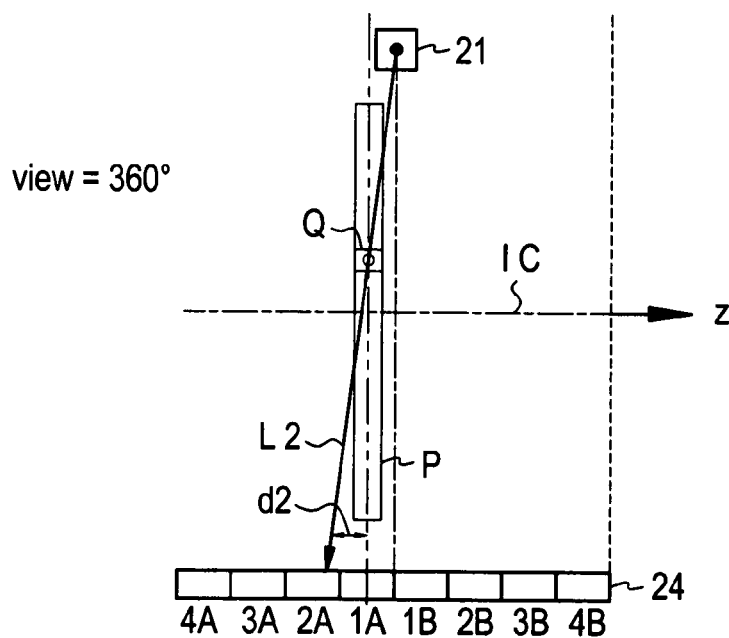
Figure 7C:
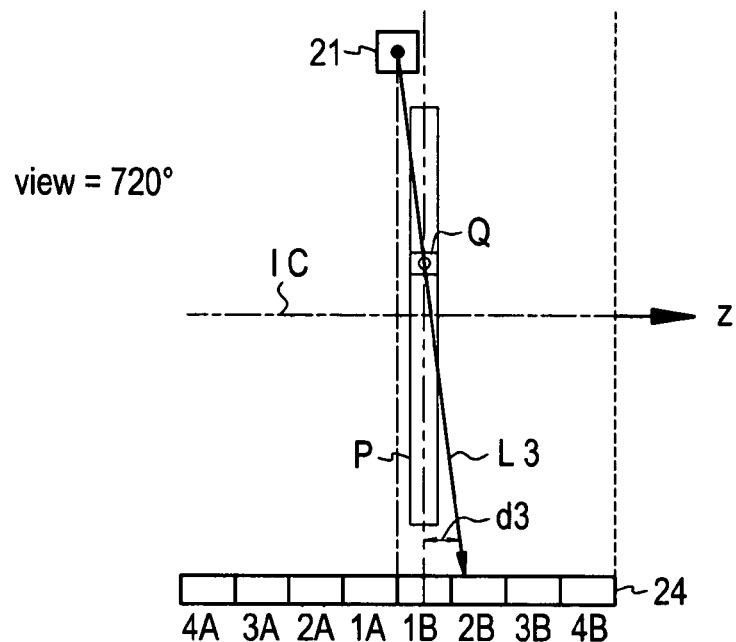
Figure 7D:
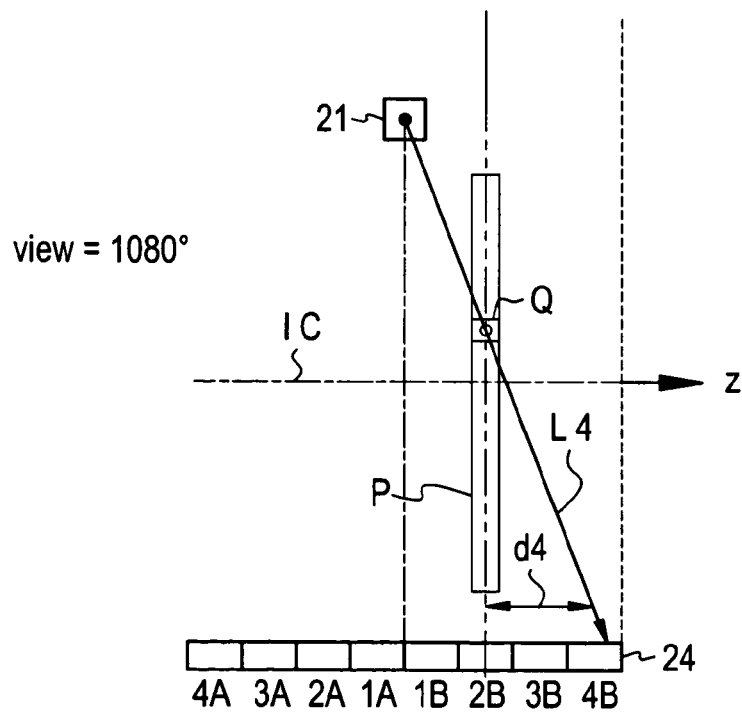

The position of the X-ray tube 21 in FIG. 9 shall correspond to the position thereof shown in FIG. 7(d).

Moreover, a projection plane pp shall be parallel to the lines L0 to L8 and passes through the center of rotation IC.

At step R3, N projection data items acquired from a selected line along different paths, along which X-rays being transmitted, with the scanner gantry set at a selected view angle are sampled. The N sampled projection data items that have been acquired from the selected line are synthesized in order to produce reconstruction projection data representing the selected line.

Figure 10:
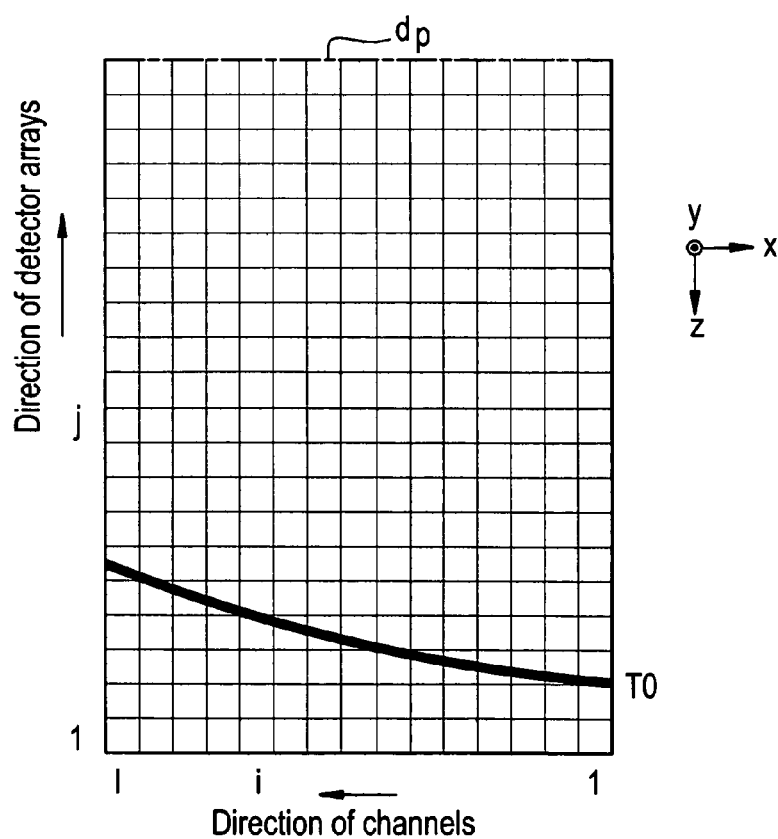
FIG. 10 is a conceptual diagram showing a line defined on a detector surface by projecting one of the lines in the scan field P.

FIG. 10 shows a line T0 defined on a detector surface dp by projecting the line L0 in the scan field P in an X-ray transmitting direction, in which X-rays are transmitted, with the X-ray tube 21 located at the position shown in FIG. 7(d).

The X-ray transmitting direction in which X-rays are transmitted is determined with the geometric positions of the X-ray tube 21, multi-channel detector 24, and line L0. With the X-ray tube 21 located at the positions shown in FIGS. 7(a), 7(b), and 7(c) respectively, in addition to FIG. 7(d), lines T0 are defined on the detector surface dp accordingly. Projection data items acquired with the scanner gantry set at the selected view angle are extracted from the detector elements identified with the detector array numbers and channel numbers indicated with the lines T0. In other words, N projection data items acquired from the selected line can be extracted. The N projection data items extracted from the same channels are weighted and summated in the same manner as those in the first embodiment. Consequently, reconstruction projection data representing one selected line and being produced based on the projection data items acquired with the scanner gantry set at the selected view angle is produced. Adopted as the position of a line defined on the detector surface dp in order to produce the reconstruction projection data is the position of a line located most closely to the scan field P among all the lines T0 defined with the plurality of projection data items.

An operator can use the input device 2 to change the setting of the number of projection data items to be synthesized N or the settings of the weights by which the N projection data items are weighted before summated.

Referring back to FIG. 8, at step R4, steps R2 to R3 are repeated relative to all lines.

Figure 11:
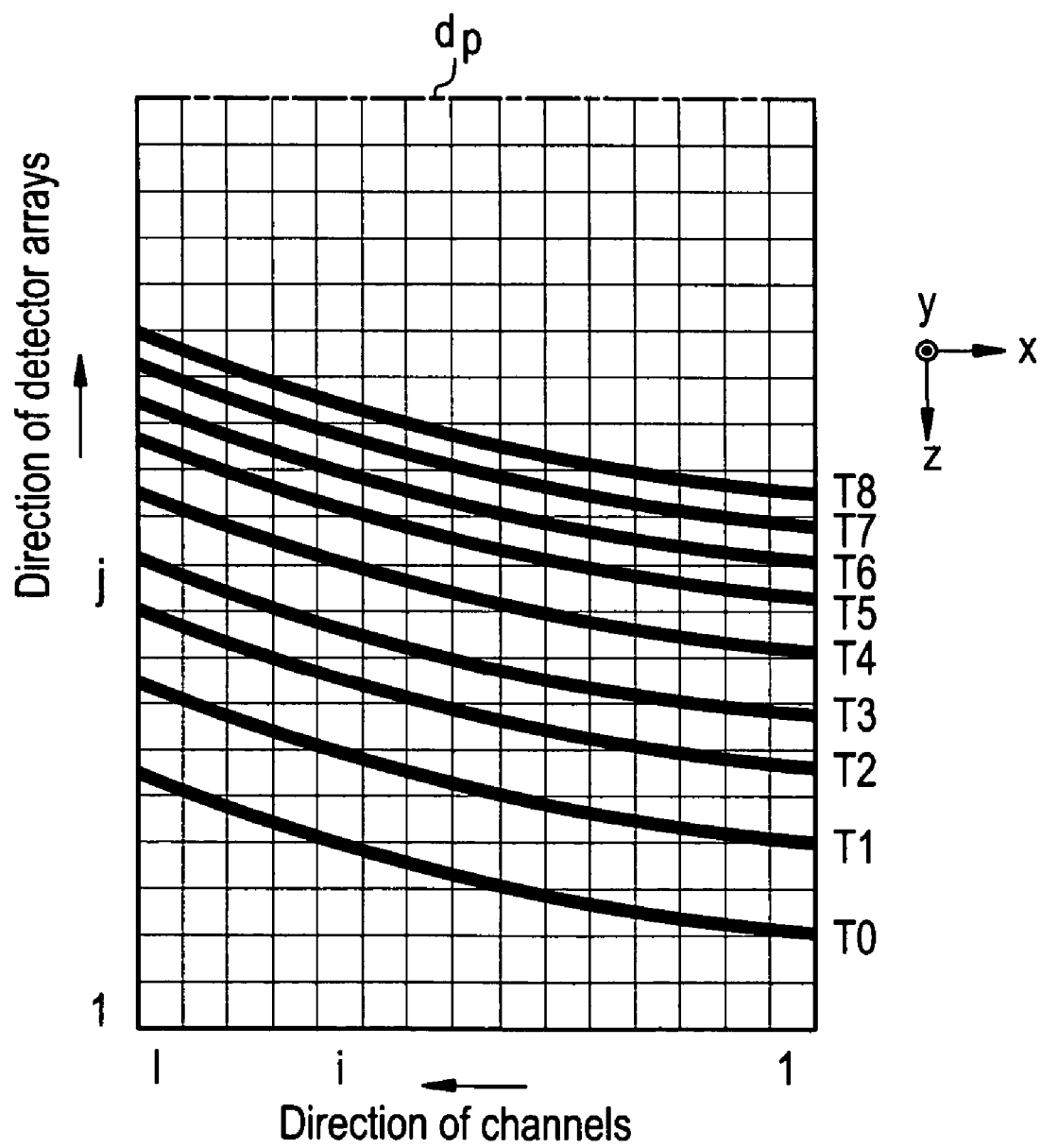
FIG. 11 is a conceptual diagram showing lines that are defined on the detector surface and that indicate reconstruction projection data items.

FIG. 11 shows lines T0 to T8 defined on the detector surface dp by projecting the lines L0 to L8 in order to produce reconstruction projection data items.

Figure 12:
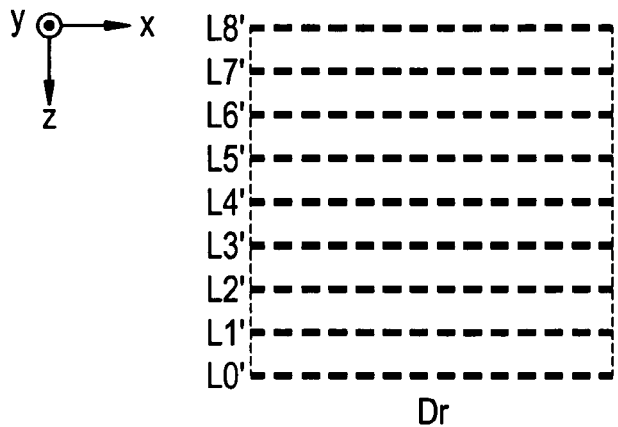
FIG. 12 is a conceptual diagram showing reconstruction projection data items Dr produced by developing the reconstruction projection data items, which are produced based on projection data items acquired with the scanner gantry set at the view angle view of 0° and extracted from the detector surface, onto a projection plane.

At step R5, as shown in FIG. 12, reconstruction projection data items produced from projection data items indicated with the lines T0 to T8 on the detector surface dp are developed as reconstruction projection data items Dr in the X-ray transmitting direction in order to define lines L0' to L8' on the projection plane pp.

Figure 13:
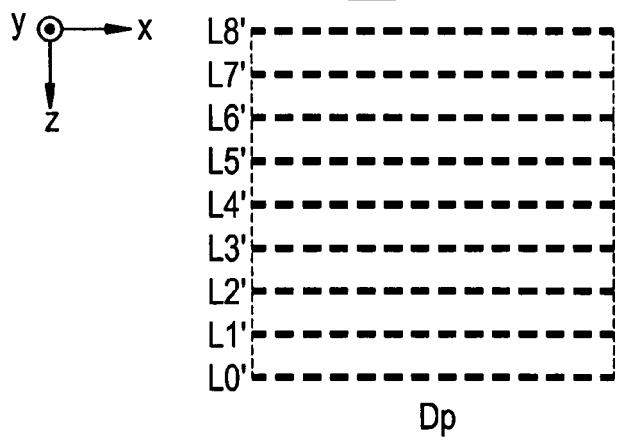
FIG. 13 is a conceptual diagram showing projection line data items Dp produced by multiplying the reconstruction projection data items Dr, which are produced based on the projection data items acquired with scanner gantry set at the view angle view of 0° and developed on the projection plane pp, by conical beam reconstruction weights.

At step R6, the reconstruction projection data items Dr indicated with the lines L0' to L8' on the projection plane pp are multiplied by conical beam reconstruction weights determined for reconstructing an image using a conical beam. This results in projection line data items Dp developed on the projection plane pp as shown in FIG. 13.

The conical beam reconstruction weights are expressed as $(r1/r0)2$ where r0 denotes the distance from the focal spot in the X-ray tube 21 to a detector element in the multi-channel detector 24 which is identified with a detector array number j and a channel number i and from which reconstruction projection data Dr is extracted, and r1 denotes the distance from the focal spot in the X-ray tube 21 to a point in the scan field P represented by the reconstruction projection data Dr.

Figure 14:
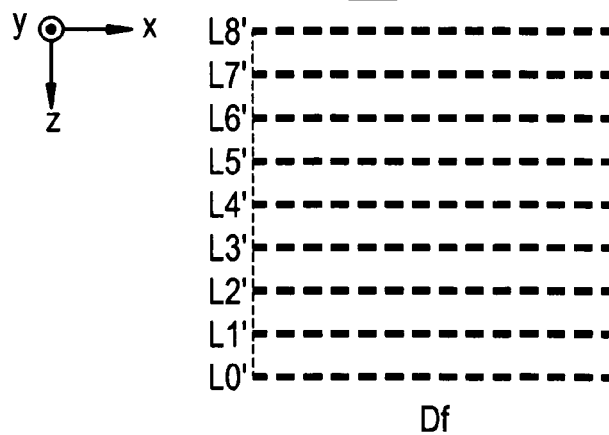
FIG. 14 is a conceptual diagram showing back projection line data items Df produced by filtering the projection line data items Dp that are produced based on the projection data items acquired with the scanner gantry set at the view angle view of 0° and developed on the projection plane pp.

At step R7, the projection line data items Dp developed on the projection plane pp are filtered. Specifically, the projection line data items Dp on the projection plane pp are fast-Fourier-transformed, multiplied by a filtering function (reconstruction function), and inverse-fast-Fourier-transformed. This results in back projection line data items Df developed on the projection plane pp as shown in FIG. 14.

Figure 15:
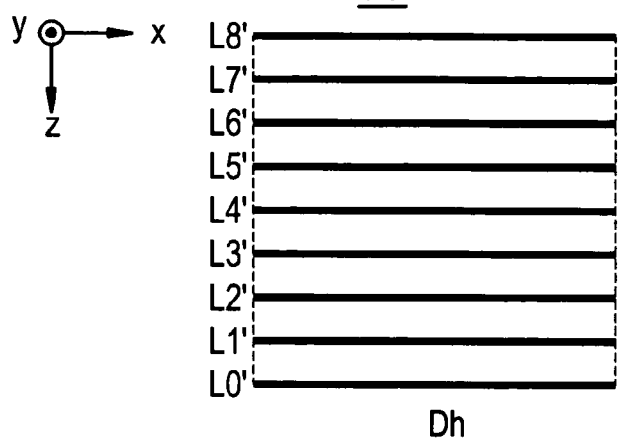
FIG. 15 is a conceptual diagram showing high-density back projection line data items Dh produced by interpolating the back projection line data items Df that are produced based on the projection data items acquired with the scanner gantry set at the view angle view of 0° and developed on the projection plane pp.
Figure 16:
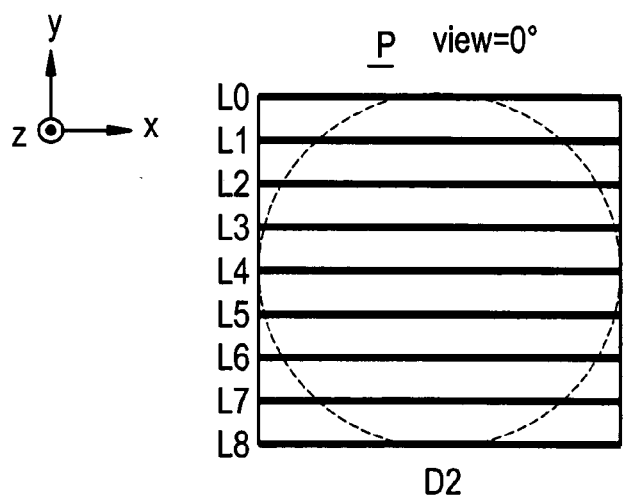
FIG. 16 is a conceptual diagram showing back projection pixel data items D2 produced by developing the high-density back projection line data items Dh, which are produced based on the projection data items acquired with the scanner gantry set at the view angle view of 0° and developed on the projection plane pp, so that the back projection pixel data items D2 will represent the pixel locations on the lines in the scan field.

At step R8, the back projection line data items Df on the projection plane pp are interpolated in the direction of lines. This results in high-density back projection line data items Dh developed on the projection plane pp as shown in FIG. 15.

The density of the high-density back projection line data items Dh on the projection plane pp is equivalent to an 8 to 32 multiple of the largest number of pixel locations in the scan field P in the direction of lines. For example, when the largest number of pixels in the scan field P is a product of 512 by 512, if the density of data items is a 16 multiple of the largest number of pixels, the density is 8192 points per line.

At step R9, the high-density back projection line data items Dh developed on the projection plane pp are sampled and, if necessary, interpolated or extrapolated. This results in back projection pixel data items D2 representing the pixel locations on the lines L0 to L8 in the scan field P.

At step R10, the high-density back projection line data items Dh developed on the projection plane pp are sampled and interpolated or extrapolated. This results in back projection pixel data items D2 representing the pixel locations on the lines L0 to L8. Otherwise, based on the back projection pixel data items D2 representing the pixel locations on the lines L0 to L8, projection data items acquired from the scan field P may be interpolated or extrapolated in order to produce back projection pixel data items D2 representing the pixel locations among the lines L0 to L8.

FIG. 12 to FIG. 17 show an image reconstruction procedure on the assumption that the view angle is equal to or larger than −45° and smaller than 45° (or falls within a range centered on the range of view angles) or equal to or larger than 135° and smaller than 225° (or falls within a range centered on the range of view angles). When the view angle is equal to or larger than 45° and smaller than 135° (or falls within a range centered on the range of view angles) or equal to or larger than 225° and smaller than 315° (or falls within a range centered on the range of view angles), an image reconstruction procedure shown in FIG. 18 to FIG. 23 is adopted. Consequently, an angle at which a line meets the X-ray transmitting direction will not be smaller than approximately 45°. Eventually, deterioration in precision can be suppressed (if a line in the scan field P is projected in the X-ray transmitting direction, as the angle at which the line meets the X-ray transmitting direction is closer to 90°, precision improves. As the angle at which the line meets the X-ray transmitting direction is closer to 0°, precision is degraded).

Figure 17:
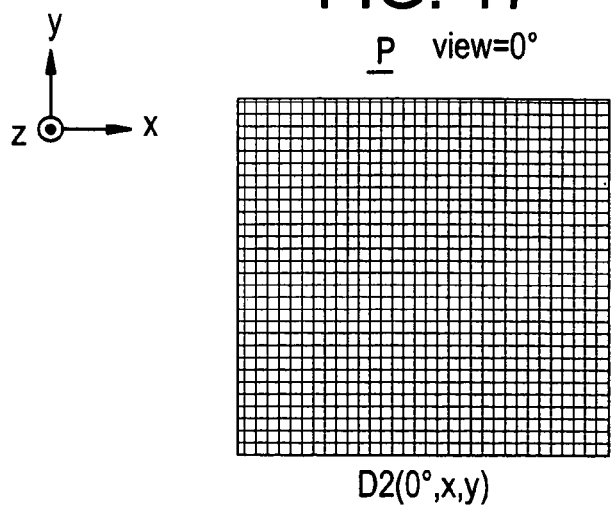
FIG. 17 is a conceptual diagram showing back projection pixel data items D2 produced by developing the high-density back projection line data items Dh, which are produced based on the projection data items acquired with the scanner gantry set at the view angle view of 0° and developed on the projection plane pp, so that the back projection pixel data items D2 will represent the pixel locations among the lines in the scan field.
Figure 18:
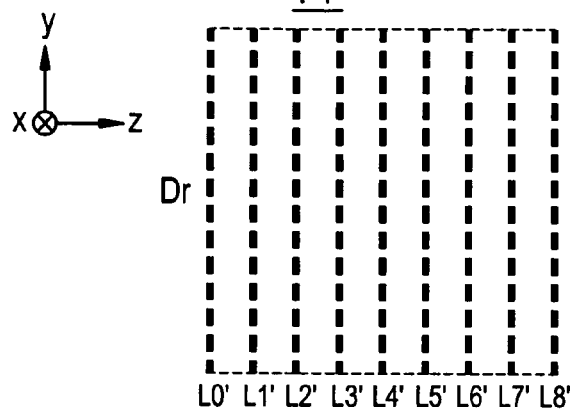
FIG. 18 is a conceptual diagram showing a state in which projection data items Dr that are indicated with lines defined on the detector surface and that are acquired with the scanner gantry set at a view angle view of 90° are developed onto the projection plane.
Figure 19:
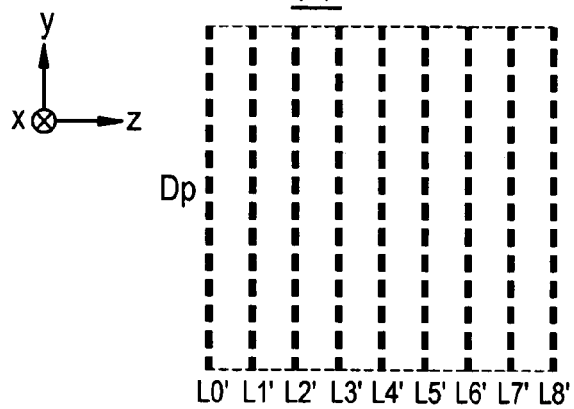
FIG. 19 is a conceptual diagram showing projection line data items Dp produced by multiplying the projection data items Dr, which are acquired with the scanner gantry set at the view angle view of 90° and developed onto the projection plane pp, by conical beam reconstruction weights.
Figure 20:
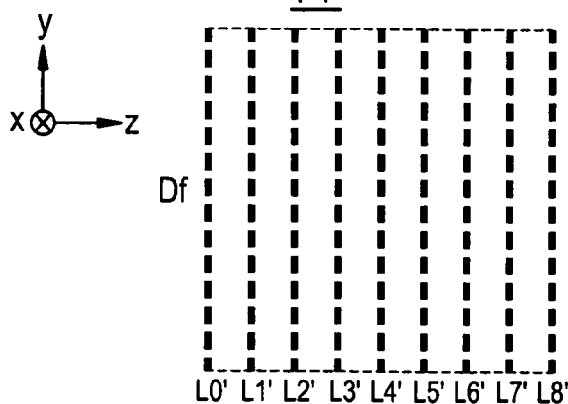
FIG. 20 is a conceptual diagram showing back projection line data items Df produced by filtering the projection line data items Dp that are produced based on the projection data items acquired with the scanner gantry set at the view angle view of 90° and developed onto the projection plane pp.
Figure 21:
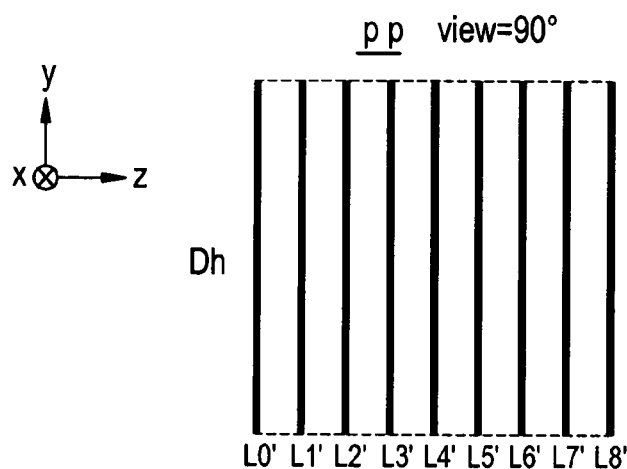
FIG. 21 is a conceptual diagram showing high-density back projection line data items Dh produced by interpolating the back projection line data items Df that are produced based on the projection data items acquired with the scanner gantry set at the view angle view of 90° and developed onto the projection plane pp.
Figure 22:
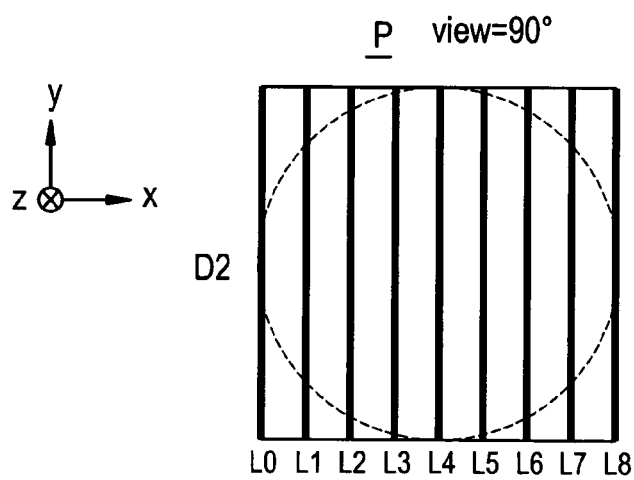
FIG. 22 is a conceptual diagram showing back projection pixel data items D2 produced by developing the high-density back projection line data items Dh, which are produced based on the projection data items acquired with the scanner gantry set at the view angle view of 90° and developed onto the projection plane pp, as if to define lines in the scan field.
Figure 23:
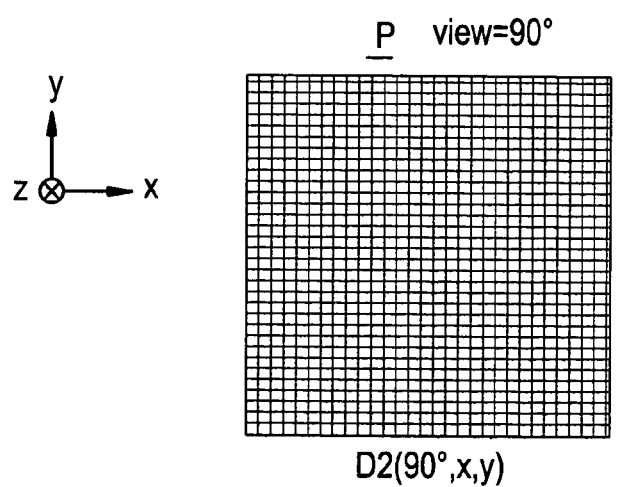
FIG. 23 is a conceptual diagram showing back projection pixel data items D2 produced by developing the high-density back projection line data items Dh, which are produced based on the projection data items acquired with the scanner gantry set at the view angle view of 90° and developed onto the projection plane pp, as if to define pixel locations among the lines in the scan field.
Figure 24:
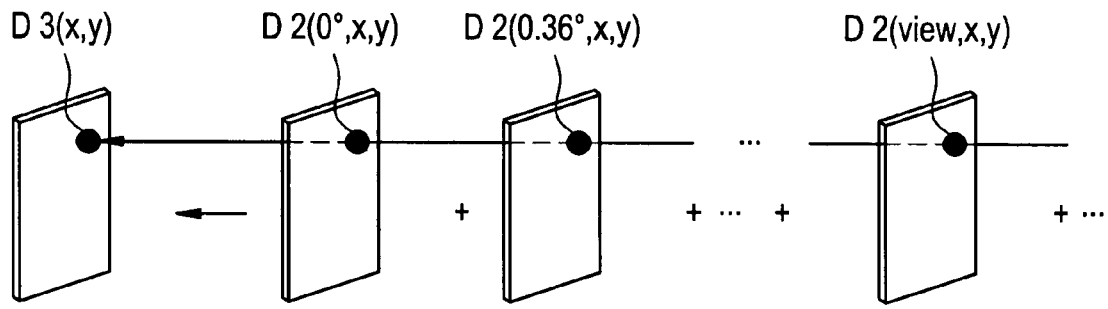
FIG. 24 is an explanatory diagram showing a state in which back projection data D3 is calculated by summating back projection pixel data items D2, which are produced based on projection data items acquired with the scanner gantry set at all view angles, pixel location by pixel location.

Referring back to FIG. 8, at step R11, as shown in FIG. 24, back projection pixel data items D2 shown in FIG. 17 or FIG. 23 are summated pixel location by pixel location.

At step R12, steps R1 to R11 are repeated relative to all view angles needed for image reconstruction. This results in back projection data items D3(x,y).

According to the X-ray CT system of the second embodiment, since pieces of information acquired along two or more different paths along which X-rays are transmitted are reflected on data relevant to one view angle, the shape of a subject can be accurately reproduced. Moreover, since the reproduction of the shape brings about little contradiction, artifact can be reduced. Moreover, since an amount of information increases, a signal-to-noise ratio improves. Furthermore, complicated arithmetic and logic operations must be performed merely on projection data items acquired from the lines L0 to L8 in the scan field P. Consequently, the number of arithmetic and logic operations to be performed can be largely reduced.

Third Embodiment

According to the first and second embodiments, projection data items acquired with the scanner gantry set at the same view angle are synthesized in order to produce reconstruction projection data items. Alternatively, projection data items acquired with the scanner gantry set at an opposite view angle may be synthesized in order to product reconstruction projection data items.

Fourth Embodiment

According to the first to third embodiments, projection data items are synthesized. Alternatively, CT images may be synthesized.

Figure 25:
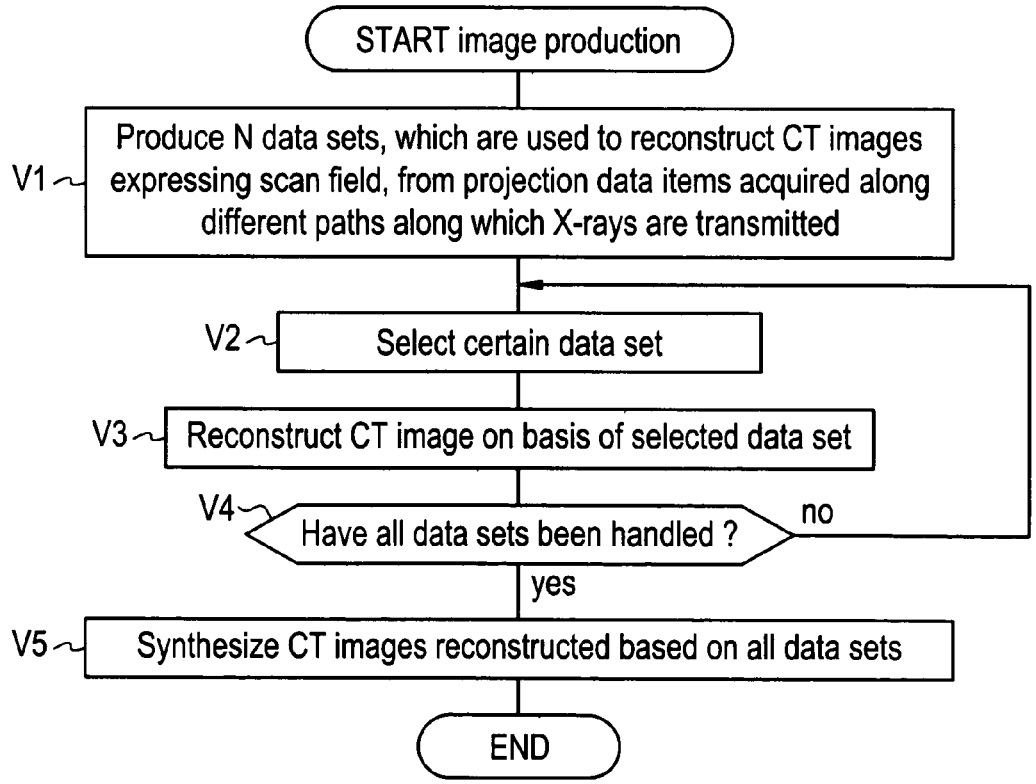
FIG. 25 is a flowchart describing image production employed in the fourth embodiment.

FIG. 25 is a flowchart describing image production employed in the fourth embodiment.

At step V1, N data sets that are used to reconstruct CT images expressing the scan field P are produced from projection data items acquired along paths along which X-rays are transmitted and some or all of which are different from one another.

For example, a first data set is produced from projection data items acquired by rotating the scanner gantry from the state attained with a view angle of 0° as shown in FIG. 7(a) to the state attained with a view angle of 360° as shown in FIG. 7(b). A second data set is produced from projection data items acquired by rotating the scanner gantry from the state attained with the view angle of 360° as shown in FIG. 7(b) to the state attained with a view angle of 720° as shown in FIG. 7(c). A third data set is produced from projection data items acquired by rotating the scanner gantry from the state attained with the view angle of 720° as shown in FIG. 7(c) to the state attained with a view angle of 1080° as shown in FIG. 7(d).

An operator can use the input device 2 to change the setting of the number of data sets N.

At step V2, a certain data set is selected.

At step V3, a CT image is reconstructed based on the selected data set.

At step V4, steps V2 and V3 are repeated relative to all data sets.

At step V5, CT images reconstructed based on all the data sets are weighted and summated in order to construct a new CT image.

Incidentally, an operator can use the input device 2 to change the settings of N weights used to weight respective CT images before summation.

According to the X-ray CT system of the fourth embodiment, since pieces of information acquired along two or more paths along which X-rays are transmitted are reflected on data relevant to one view angle, the shape of a subject can be accurately reproduced. Moreover, since the reproduction of the shape brings about little contradiction, artifact can be reduced. Moreover, since an amount of information increases, a signal-to-noise ratio improves. Furthermore, a plurality of CT images expressing the same scan field P can be reconstructed simultaneously.

Fifth Embodiment

Any of the three-dimensional image reconstruction methods proposed in Japanese Patent Applications Nos. 2002-066420, 2002-147061, 2002-147231, 2002-235561, 2002-235662, 2002-267833, 2002-322756, and 2002-338947 may be adopted as an image reconstruction method.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT image production method, comprising the steps of:
    acquiring projection data while relatively rotating at least one of an X-ray tube and a multi-channel detector about a subject and relatively rectilinearly moving the subject;
    combining a first projection data item with a second projection data item, wherein the first and second projection data items are acquired with X-rays that pass through the same pixel location of the same reconstruction plane while being transmitted along different paths with a scanner gantry set at the same view angle or an opposite view angle, so as to produce reconstruction projection data relevant to the view angle; and
    reconstructing a CT image on the basis of the reconstruction projection data.

2. An X-ray CT image production method according to claim 1, wherein the first and second projection data items are weighted and summated, to thereby produce the reconstruction projection data.

3. An X-ray CT image production method according to claim 2, wherein as the distances of detector arrays, which detect the first and second projection data items respectively, from the reconstruction plane are shorter, weights to be used for the weighting and summation are made larger.

4. An X-ray CT image production method according to claim 2, wherein an operator designates the weights to be used for the weighting and summation.

5. An X-ray CT image production method according to claim 1, wherein an operator designates a number of projection data items N that is larger than 2 and that are acquired by rotating the X-ray tube.

6. An X-ray CT system, comprising:
    an X-ray tube;
    a multi-channel detector;
    a helical scan device for acquiring projection data while relatively rotating at least one of said X-ray tube and said multi-channel detector about a subject and relatively rectilinearly moving the subject;
    a reconstruction projection data production device configured to combine a first projection data item with a second projection data item, wherein the first and second projection data items are acquired with X-rays that pass through the same pixel location of the same reconstruction plane while being transmitted along different paths with a scanner gantry set at the same view angle or an opposite view angle, so as to produce reconstruction projection data relevant to the view angle; and
    an image reconstruction device for reconstructing a CT image on the basis of the reconstruction projection data.

7. An X-ray CT system according to claim 6, wherein said reconstruction projection data production device weights and summates the first and second projection data items, to thereby produce the reconstruction projection data.

8. An X-ray CT system according to claim 7, wherein as the distances of detector arrays, which detect the first and second respective projection data items, from the reconstruction plane are shorter, said reconstruction projection data production device makes weights, which are used for the weighting and summation, larger.

9. An X-ray CT system according to claim 7, further comprising a designation device for allowing an operator to designate the weights that are used for the weighting and summation.

10. An X-ray CT system according to claim 6, further comprising a designation device for allowing an operator to designate a number of projection data items N that is larger than 2 and that are acquired by rotating said X-ray tube.

11. An X-ray CT system, comprising:
    an X-ray tube;
    a multi-channel detector;
    a helical scan device for acquiring projection data while relatively rotating at least one of said X-ray tube and said multi-channel detector about a subject and relatively rectilinearly moving the subject;
    a data set production device for producing two or more data sets that are used to reconstruct CT images expressing the same reconstruction plane;
    an image reconstruction device for reconstructing two or more CT images on the basis of the two or more data sets; and
    an image synthesis device for combining the CT images so as to construct a synthetic CT image.

12. An X-ray CT system according to claim 11, wherein said image synthesis device weights and summates the two or more CT images so as to construct the synthetic CT image.

13. An X-ray CT system according to claim 12, wherein as the distances of detector arrays, via which the respective data sets are produced, from the reconstruction plane are shorter, said image synthesis device makes the weights, which are used for the weighting and summation, larger.

14. An X-ray CT system according to claim 12, further comprising a designation device for allowing an operator to designate the weights that are used for the weighting and summation.

15. An X-ray CT system according to claim 11, further comprising a designation device for allowing an operator to designate the number of data sets N that is larger than 2.

16. An X-ray CT image production method according to claim 1, wherein said reconstructing a CT image comprises reconstructing a three-dimensional CT image.

* * * * *